(12) United States Patent
Palese (10) Patent No.: US 10,201,344 B2
(45) Date of Patent: Feb. 12, 2019

(54) KNOTLESS SUTURE ANCHOR AND METHOD OF USING SAME

(71) Applicant: Biomet Sports Medicine, LLC, Warsaw, IN (US)

(72) Inventor: Christopher Palese, South Whitley, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 231 days.

(21) Appl. No.: 15/210,248

(22) Filed: Jul. 14, 2016

(65) Prior Publication Data

US 2016/0317143 A1    Nov. 3, 2016

Related U.S. Application Data

(62) Division of application No. 13/791,061, filed on Mar. 8, 2013, now Pat. No. 9,414,834.

(51) Int. Cl.
*A61B 17/04* (2006.01)
*A61F 2/08* (2006.01)

(52) U.S. Cl.
CPC .. *A61B 17/0401* (2013.01); *A61B 2017/0409* (2013.01); *A61B 2017/0414* (2013.01);
(Continued)

(58) Field of Classification Search
CPC ........ A61B 17/0401; A61B 2017/0409; A61B 2017/0412; A61B 2017/0414; A61B 2017/042; A61B 2017/0422; A61B 2017/0424; A61B 2017/0425; A61B 2017/0427; A61B 2017/0429; A61B 2017/043; A61B 2017/0432; A61B 2017/0433; A61B 2017/0437;
(Continued)

(56) References Cited

U.S. PATENT DOCUMENTS 4,738,255 A * 4/1988 Goble ............... A61B 17/0401
                                                    29/243.519
5,324,308 A    6/1994 Pierce
(Continued)

OTHER PUBLICATIONS

"U.S. Appl. No. 13/791,061, Advisory Action dated Nov. 10, 2015", 3 pgs.
(Continued)

*Primary Examiner* — Ryan J Severson
(74) *Attorney, Agent, or Firm* — Schwegman Lundberg & Woessner, P.A.

(57) ABSTRACT

A suture anchor including an outer anchor part and an inner anchor part. The outer anchor part includes a proximal end, a distal end, and an inner surface defining a center bore extending between the proximal end and the distal end. The center bore includes a tapered proximal portion. The inner anchor part includes a tapered outer surface defining a first pair of opposing apertures. Insertion of the inner anchor part into the tapered proximal portion of the outer anchor part enables a suture extending through the first pair of opposing apertures to be coupled to the suture anchor. A taper fit between the tapered proximal portion of the center bore of the outer anchor part and the tapered outer surface of the inner anchor part retains the inner anchor part within the outer anchor part.

15 Claims, 5 Drawing Sheets

(52) U.S. Cl.
CPC ............... *A61B 2017/0424* (2013.01); *A61B 2017/0425* (2013.01); *A61B 2017/0432* (2013.01); *A61B 2017/0445* (2013.01); *A61B 2017/0464* (2013.01); *A61F 2002/0823* (2013.01); *A61F 2002/0888* (2013.01)

(58) Field of Classification Search
CPC .... A61B 2017/0438; A61B 2017/0448; A61B 2017/0446; A61B 2017/045; A61B 2017/0451; A61B 2017/0456; A61B 2017/0459; A61F 2/0811; A61F 2002/0817; A61F 2002/0823; A61F 2002/0835; A61F 2002/0841; A61F 2002/0876; A61F 2002/0888
See application file for complete search history.

(56) References Cited

U.S. PATENT DOCUMENTS

| | | | |
|---|---|---|---|
| 5,383,905 A * | 1/1995 | Golds | A61B 17/0487 24/136 L |
| 5,443,482 A * | 8/1995 | Stone | A61B 17/0401 606/232 |
| 5,643,321 A | 7/1997 | McDevitt | |
| 5,645,589 A | 7/1997 | Li et al. | |
| 5,649,963 A | 7/1997 | Mcdevitt | |
| 5,679,723 A | 10/1997 | Cooper | |
| 5,725,529 A | 3/1998 | Nicholson et al. | |
| 5,797,963 A | 8/1998 | Mcdevitt | |
| 5,814,071 A | 9/1998 | Mcdevitt et al. | |
| 5,911,721 A | 6/1999 | Nicholson et al. | |
| 5,968,044 A | 10/1999 | Nicholson et al. | |
| 6,129,762 A | 10/2000 | Li | |
| 6,468,293 B2 * | 10/2002 | Bonutti | A61B 17/0487 606/148 |
| 6,524,316 B1 | 2/2003 | Nicholson et al. | |
| 7,674,276 B2 | 3/2010 | Stone et al. | |
| 7,713,285 B1 | 5/2010 | Stone et al. | |
| 7,976,565 B1 | 7/2011 | Meridew | |
| 8,162,978 B2 | 4/2012 | Lombardo et al. | |
| 8,409,252 B2 | 4/2013 | Lombardo et al. | |
| 8,512,405 B2 | 8/2013 | Baird | |
| 8,574,275 B2 * | 11/2013 | Stone | A61B 17/0401 606/313 |
| 8,758,406 B2 * | 6/2014 | Fanton | A61B 17/0401 606/232 |
| 8,870,933 B2 | 10/2014 | Aeschlimann et al. | |
| 8,986,345 B2 * | 3/2015 | Denham | A61B 17/0401 606/232 |
| 9,192,371 B2 * | 11/2015 | Palese | A61B 17/0401 |
| 9,414,834 B2 * | 8/2016 | Palese | A61B 17/0401 |
| 9,445,888 B2 * | 9/2016 | Aeschlimann | A61B 17/0401 |
| 9,463,009 B2 * | 10/2016 | Sack | A61B 17/844 |
| 2001/0021862 A1 * | 9/2001 | Bonutti | A61B 17/0487 606/232 |
| 2006/0235413 A1 | 10/2006 | Denham et al. | |
| 2008/0097604 A1 | 4/2008 | Strobel et al. | |
| 2008/0109080 A1 | 5/2008 | Aeschlimann et al. | |
| 2008/0275469 A1 | 11/2008 | Fanton et al. | |
| 2009/0248068 A1 | 10/2009 | Lombardo et al. | |
| 2009/0318964 A1 | 12/2009 | Lombardo et al. | |
| 2010/0262185 A1 * | 10/2010 | Gelfand | A61B 17/0401 606/232 |
| 2011/0004258 A1 * | 1/2011 | Stone | A61B 17/0401 606/329 |
| 2011/0166599 A1 | 7/2011 | Jervis et al. | |
| 2014/0025125 A1 | 1/2014 | Sack et al. | |
| 2014/0257355 A1 | 9/2014 | Palese | |
| 2014/0257381 A1 | 9/2014 | Palese | |
| 2015/0012095 A1 | 1/2015 | Aeschlimann et al. | |
| 2016/0022260 A1 * | 1/2016 | Palese | A61B 17/0401 606/232 |
| 2016/0317143 A1 * | 11/2016 | Palese | A61B 17/0401 |

OTHER PUBLICATIONS

"U.S. Appl. No. 13/791,061, Final Office Action dated Sep. 2, 2015", 12 pgs.
"U.S. Appl. No. 13/791,061, Non Final Office Action dated Mar. 3, 2015", 16 pgs.
"U.S. Appl. No. 13/791,061, Non Final Office Action dated Dec. 15, 2015", 12 pgs.
"U.S. Appl. No. 13/791,061, Notice of Allowance dated Apr. 19, 2016", 7 pgs.
"U.S. Appl. No. 13/791,061, Response filed Mar. 15, 2016 to Non Final Office Action dated Dec. 15, 2015", 15 pgs.
"U.S. Appl. No. 13/791,061, Response filed Aug. 3, 2015 to Non Final Office Action dated Mar. 3, 2015", 11 pgs.
"U.S. Appl. No. 13/791,061, Response filed Nov. 2, 2015 to Final Office Action dated Sep. 2, 2015", 13 pgs.
"U.S. Appl. No. 13/791,061, Response filed Nov. 18, 2015 to Final Office Action dated Sep. 2, 2015", 13 pgs.

* cited by examiner

KNOTLESS SUTURE ANCHOR AND METHOD OF USING SAME

CLAIM OF PRIORITY

This application is a divisional of U.S. patent application Ser. No. 13/791,061, filed on Mar. 8, 2013, the benefit of priority of which is claimed hereby, and which is incorporated by reference herein in its entirety.

FIELD

The present disclosure relates to a knotless suture anchor and a method of using the knotless suture anchor.

BACKGROUND

This section provides background information related to the present disclosure, which is not necessarily prior art.

Surgeons often use suture to secure bone and tissue in place during a surgical procedure. The suture can be retained in place with a suture anchor, which is typically implanted in bone. The suture can be connected to the tissue or bone either before or after the anchor is implanted. The suture is often connected to the anchor with a knot, which can be difficult to tie during surgery. The present teachings eliminate the need for connecting the suture to the anchor with a knot by providing for a knotless suture anchor and method of using the knotless suture anchor.

SUMMARY

This section provides a general summary of the disclosure, and is not a comprehensive disclosure of its full scope or all of its features.

The present teachings provide for a suture anchor including an outer anchor part and an inner anchor part. The outer anchor part includes a proximal end, a distal end, and an inner surface defining a center bore extending between the proximal end and the distal end. The center bore includes a tapered proximal portion. The inner anchor part includes a tapered outer surface defining a first pair of opposing apertures. Insertion of the inner anchor part into the tapered proximal portion of the outer anchor part enables a suture extending through the first pair of opposing apertures to be coupled to the suture anchor. A taper fit between the tapered proximal portion of the center bore of the outer anchor part and the tapered outer surface of the inner anchor part retains the inner anchor part within the outer anchor part.

The present teachings further provide for a method of implanting a suture anchor into a bone hole. The method includes inserting a suture anchor into the bone hole with an inserter. The suture anchor includes an outer anchor part and an inner anchor part that are decoupled during insertion. The method further includes coupling the outer anchor part and the inner anchor part with a taper lock between a tapered outer surface of the inner anchor part and a tapered inner surface of the outer anchor part. A suture extending through a first pair of opposing apertures defined in the inner anchor part is compressed between the outer anchor part and the inner anchor part to retain the suture to the suture anchor.

The present teachings also provide a system for implanting a suture anchor in a bone hole. The insertion tool includes an elongated rod having a first coupling member proximate to a distal end thereof. An outer anchor part of the suture anchor defines a first center bore configured to receive the elongated rod. The first center bore includes a tapered proximal portion and a distal portion including a second coupling member configured to cooperate with the first coupling member of the insertion tool to couple the outer anchor part to the insertion tool. An inner anchor part of the suture anchor includes a tapered outer surface. The inner anchor part defines both a first pair of opposing apertures and a second center bore configured to receive the elongated rod to support the inner anchor part on the elongated rod at a proximal end of the outer anchor part. The insertion tool is configured to insert the inner anchor part within the outer anchor part such that the tapered outer surface of the inner anchor part contacts the tapered proximal portion of the outer anchor part to form a taper lock therebetween, and enable a suture extending through the first pair of opposing apertures to be coupled to the suture anchor by trapping the suture between the outer and inner anchor parts.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
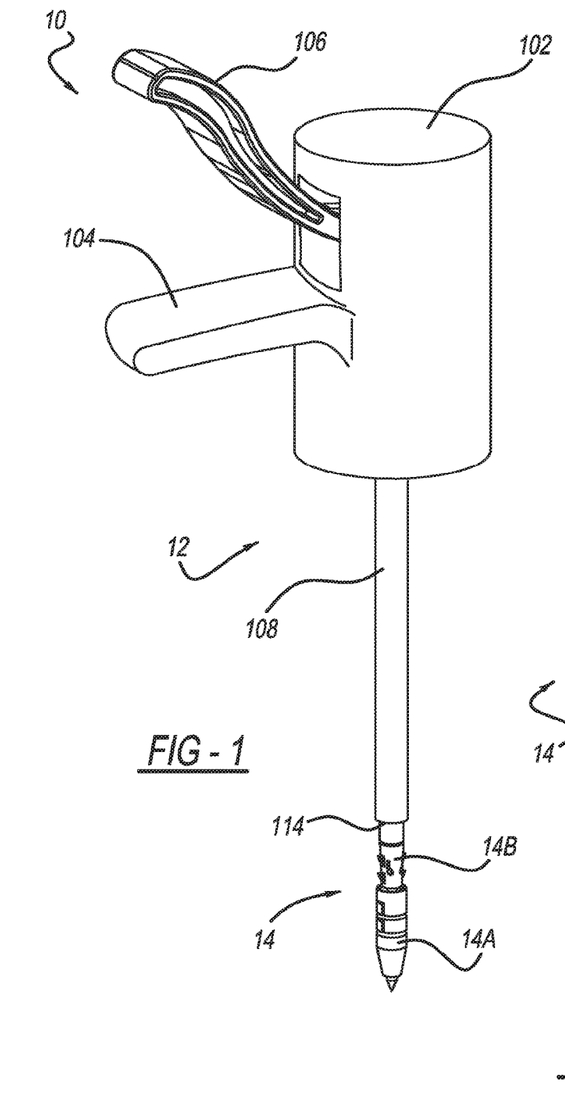
FIG. 1 is a perspective view of a knotless suture anchor assembly according to the present teachings, the assembly generally includes an insertion tool and a suture anchor.

With initial reference to FIG. 1, a knotless suture anchor assembly according to the present teachings is generally illustrated at reference numeral 10. The knotless suture anchor assembly 10 generally includes an insertion tool 12 and a suture anchor 14. With additional reference to FIGS. 2-4, the suture anchor 14 includes an outer or first portion 14A and an inner or second portion 14B.

Figure 3:
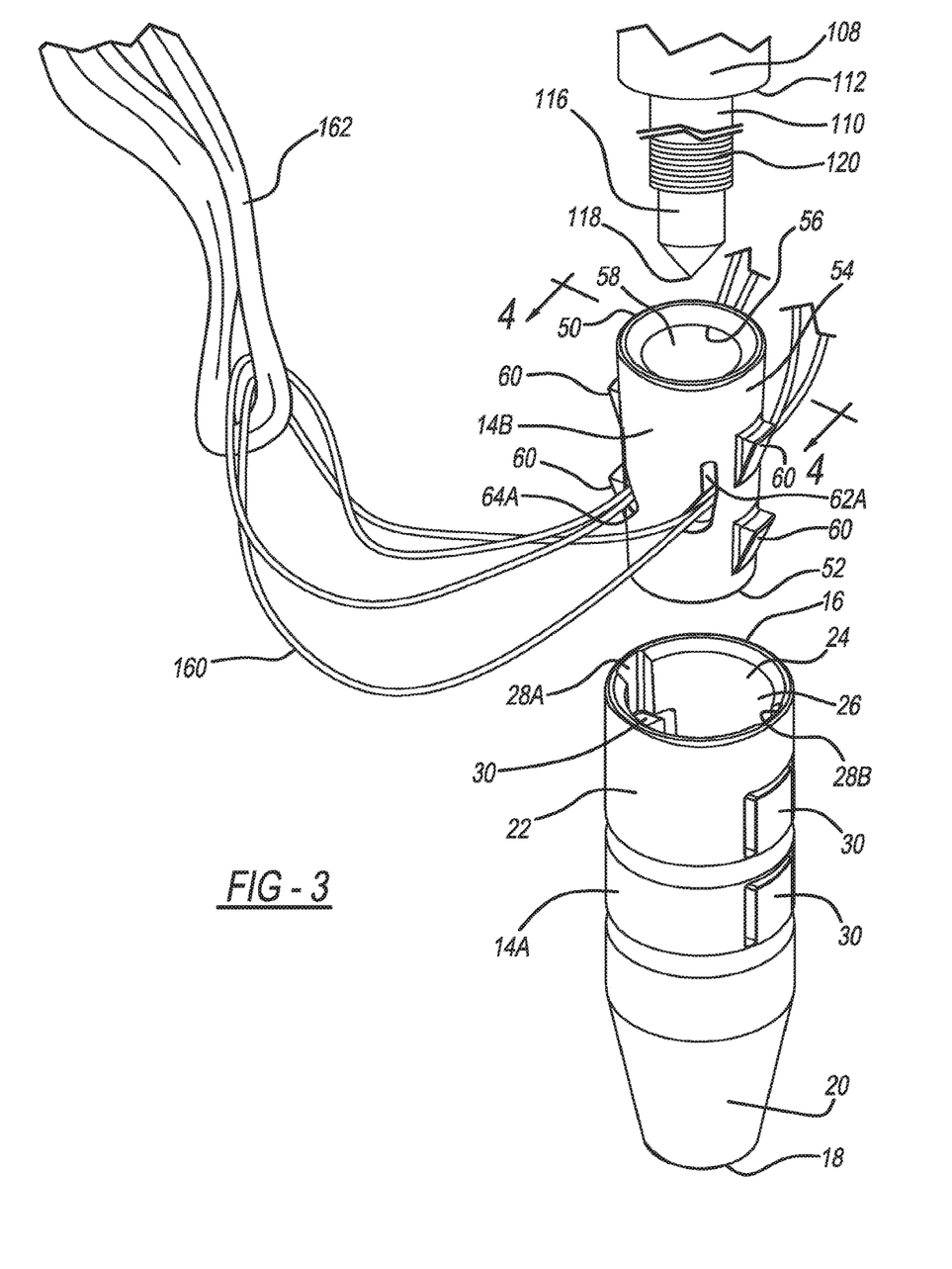
FIG. 3 is another perspective view of the suture anchor and a distal portion of the insertion tool, a suture attached to tissue is threaded through an inner portion of the suture anchor.
Figure 4:
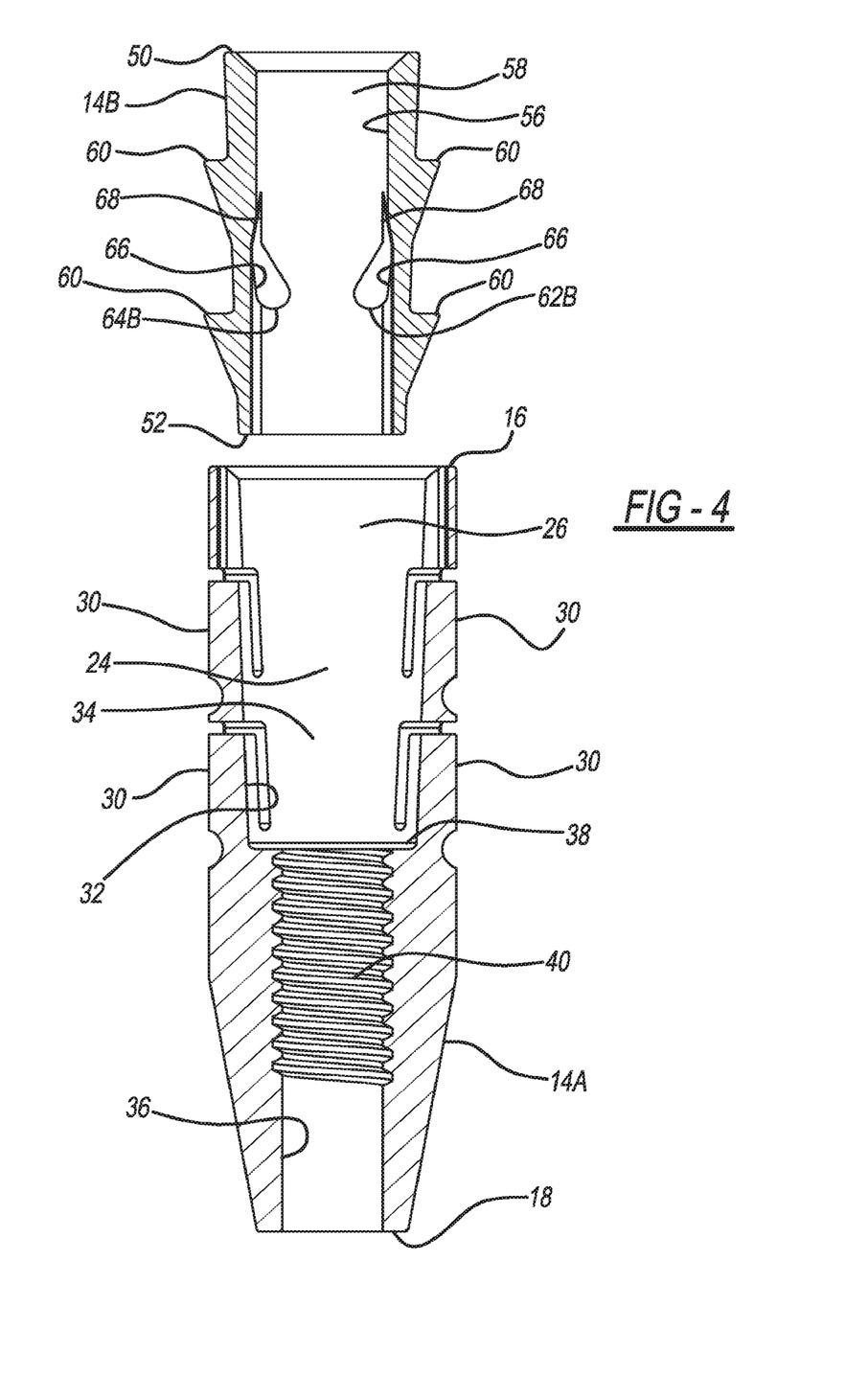
FIG. 4 is a cross-sectional view of the suture anchor of FIGS. 1-3.

With particular reference to FIGS. 3 and 4, the outer portion 14A includes a proximal end 16 and a distal end 18, which is opposite to the proximal end 16. At the distal end 18 is a conical or tapered tip 20 having a blunt end. The outer portion 14A includes an outer surface 22 and an inner surface 24. Both the outer surface 22 and the inner surface 24 extend between the proximal end 16 and the distal end 18.

The inner surface 24 defines a first bore 26, which is a center bore. The first bore 26 extends between the proximal end 16 and the distal end 18. The inner surface 24 defines a first slot 28A and a second opposed slot 28B, which both extend from the proximal end 16. The first slot 28A is opposite to the second slot 28B. The first and second slots 28A and 28B extend to retention fins 30.

The retention fins 30 are portions of the outer portion 14A that are expandable outward from the outer surface 22 upon implantation of the outer portion 14A in bone in order to retain the outer portion 14A in bone, as described in detail herein. Although four retention fins 30 are illustrated, with two on opposing sides of the outer portion 14A and axially spaced apart, any suitable number of retention fins 30 can be provided. Further, any member suitable for coupling to bone can be included with the outer portion 14A in order to retain the outer portion 14A in bone once implanted.

With particular reference to FIG. 4, the inner surface 24 also includes a tapered proximal portion 32 of the first bore 26. At the tapered proximal portion 32, the inner surface 24 includes a tapered sidewall 34. The tapered sidewall 34 gradually tapers inward from the proximal end 16 to a distal portion 36 of the first bore 26. The distal portion 36 is defined by the inner surface 24 and extends from the proximal portion 32 to the distal end 18 of the outer portion 14A. The distal portion 36 is generally linear and not tapered. The distal portion 36 is also narrower than the tapered proximal portion 32. Therefore, an internal flange 38 is defined by the inner surface 24 between the tapered proximal portion 32 and the distal portion 36.

At the distal portion 36, the inner surface 24 includes a first locking or coupling member 40. The first locking member 40 can be any suitable coupling member for coupling the outer portion 14A to the insertion tool 12. For example, the first locking member 40 can include threads defined in the inner surface 24 and a non-threaded portion.

Features of the inner portion 14B of the suture anchor 14 will now be described. The inner portion 14B generally includes a proximal end 50 and a distal end 52, which is opposite to the proximal end 50. Extending between the proximal end 50 and the distal end 52 is a tapered outer surface 54 and an inner surface 56. The inner surface 56 is opposite to the tapered outer surface 54. The inner surface 56 defines a second or center bore 58. The inner surface 56, and thus the second bore 58 as well, extends generally linearly between the proximal end 50 and the distal end 52.

Protruding from the tapered outer surface 54 are a plurality of ramped retention tabs 60. Although four retention tabs 60 are illustrated, with two on opposing sides of the tapered outer surface 54 and axially spaced apart, any suitable number of retention tabs 60 can be provided. The retention tabs 60 are generally rigid, and their number and location corresponds to the number and location of the retention fins 30 of the outer portion 14A, such that upon insertion of the inner portion 14B into the outer portion 14A, as described in detail herein, the retention tabs 60 pass through the first and second slots 28A and 28B in order to contact the retention fins 30 and pivotably or hingingly force the retention fins 30 outward from the outer surface 22 to a deployed position.

The tapered outer surface 54 and the inner surface 56 of the inner portion 14B define a first pair of apertures 62A and 62B, and a second pair of apertures 64A and 64B. The first pair of apertures 62A and 62B are aligned with one another on opposite sides of the inner portion 14B. Similarly, the second pair of apertures 64A and 64B are aligned on opposite sides of the inner portion 14B. The first pair of apertures 62A/62B generally define a first suture passageway through the inner portion 14B. The second pair of apertures 64A/64B generally define a second suture passageway through the inner portion 14B. The first and second suture passageways are spaced apart and are arranged generally parallel to one another.

Each of the apertures 62A, 62B, 64A, and 64B include a first portion 66 and a second portion 68 to provide each of the apertures generally with a "tear drop" shape. The first and second portions 66 and 68 are connected to one another. The first portion 66 is larger than the second portion 68. More specifically, the second portion 68 is more narrow than the first portion 66. The second portion 68 is generally sized such that when a suture is moved from the first portion 66 to the second portion 68, the suture will be pinched in the second portion 68 thereby restricting movement of the suture through the second portion 68.

The suture anchor 14 can be made of any suitable biocompatible material, such as a suitable metallic or polymer. Exemplary polymers include polyether ether ketone (PEEK) and polyether ketone (PEK).

With reference to FIG. 3, prior to implantation of the suture anchor 14, one or more suitable sutures, such as suture 160, can be threaded through the first pair of apertures 62A/62B and the second pair of apertures 64A/64B. More specifically, the suture 160 can be threaded through the suture passageway defined by the apertures 62A and 62B such that it extends through each of the apertures 62A and 62B using a suitable insertion device, such as a Nitinol threader. Similarly, the suture 160 can be threaded through the suture passageway defined by the apertures 64A and 64B.

The suture 160 is threaded through the first portion 66 of each of the apertures 62A, 62B, 64A, and 64B. The first portion 66 has a diameter larger than that of the suture 160, and thus the suture 160 is free to be maneuvered through the apertures 62A, 62B, 64A, and 64B in order to adjust the suture 160 and tension the tissue 162. The suture 160 can be threaded through the apertures 62A, 62B, 64A, and 64B either before or after the inner portion 14B is mounted to the insertion tool 12. Before or after threading the suture 160 through the apertures 62A, 62B, 64A, and 64B, the suture 160 can be connected to any suitable tissue or bone to be anchored, such as the tissue 162.

Figure 2:
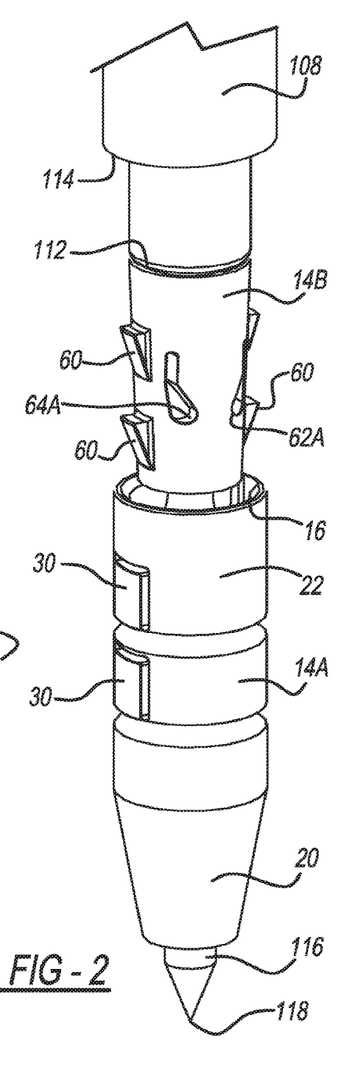
FIG. 2 is a perspective view of the suture anchor and a distal portion of the insertion tool.
Figure 5:
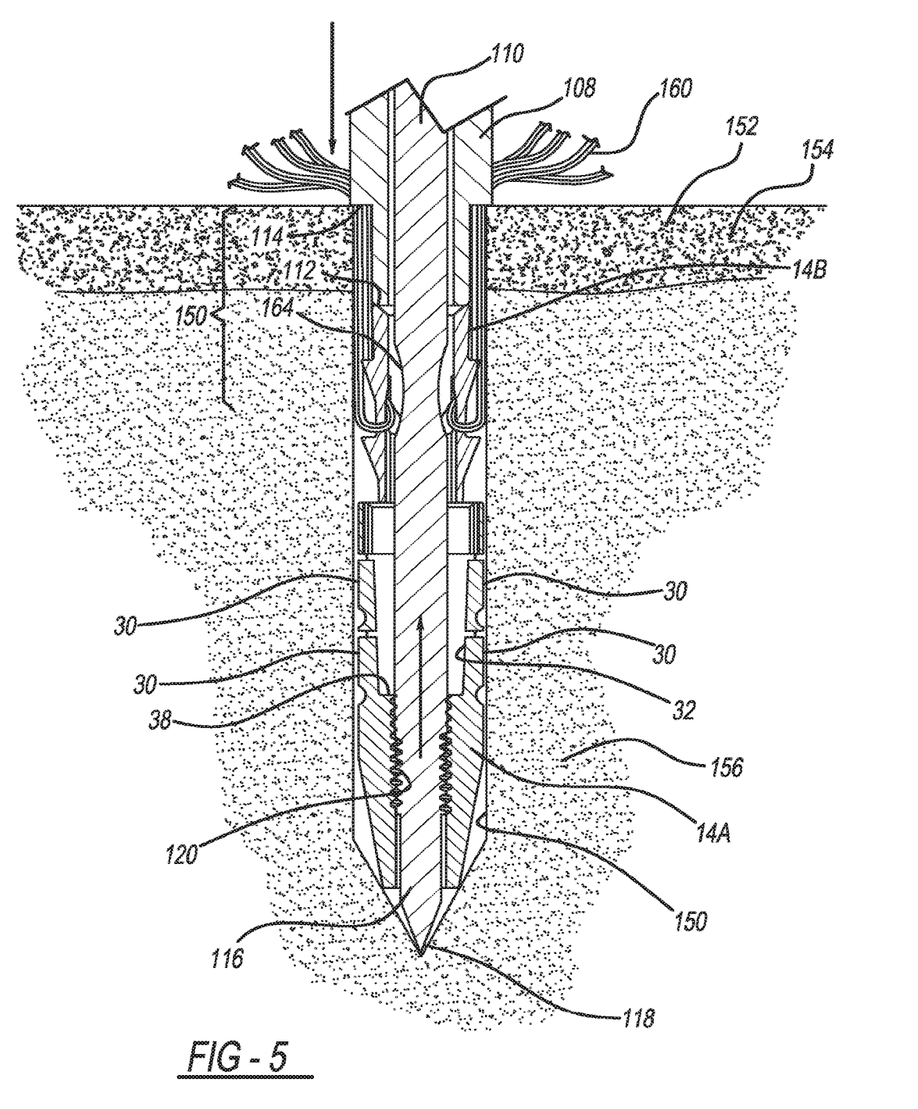
FIG. 5 is a cross-sectional view of the suture anchor being inserted into bone using the insertion tool.

With reference to FIGS. 1-3, features of the insertion tool 12 will now be described. The insertion tool 12 generally includes a body 102 with a handle 104 and a lever 106. Extending from the body 102 is an elongated shaft 108. Within the elongated shaft 108 is an inner rod 110 (FIGS. 3 and 5). The inner rod 110 is movable within the elongated shaft 108 upon actuation of the lever 106. Actuation of the lever 106 draws the inner rod 110 proximally toward the body 102.

The inner rod 110 extends beyond a distal end 112 of the elongated shaft 108. The inner rod 110 includes a distal end 116 with a pointed tip 118. Proximate to the distal end 116, the inner rod 110 includes a second locking member 120. The second locking member 120 can include any suitable feature for coupling with the first locking member 40 of the outer portion 14A, such as threads. The elongated shaft 108 defines an annular flange 114 proximate to, but spaced apart from, the distal end 112. Both the elongated shaft 108 and the inner rod 110 are generally rigid.

The suture anchor is coupled to the insertion tool 12 such that the proximal end 50 of the inner portion 14B abuts, or is proximate to, the distal end 112 of the elongated shaft 108. The inner rod 110 of the insertion tool 12 extends through the second bore 58 of the inner portion 14B and into the first bore 26 of the outer portion 14A. The distal end 116 and the pointed tip 118 of the inner rod 110 protrude from the second bore 58 at the distal end 18 of the outer portion 14A. The second locking member 120 of the inner rod 110 couples with the first locking member 40 to retain the outer portion 14A on the inner rod 110. The second locking member 120 can threadably engage the first locking member 40 when the first and second locking members 40 and 120 include threads. The inner portion 14B is thus retained between the outer portion 14A and the elongated shaft 108. The inner rod 110 has a diameter 164 such that a suture 160 can extend around the inner rod 110 through the first pair of apertures 62A/62B and the second pair of apertures 64A/64B.

Figure 6:
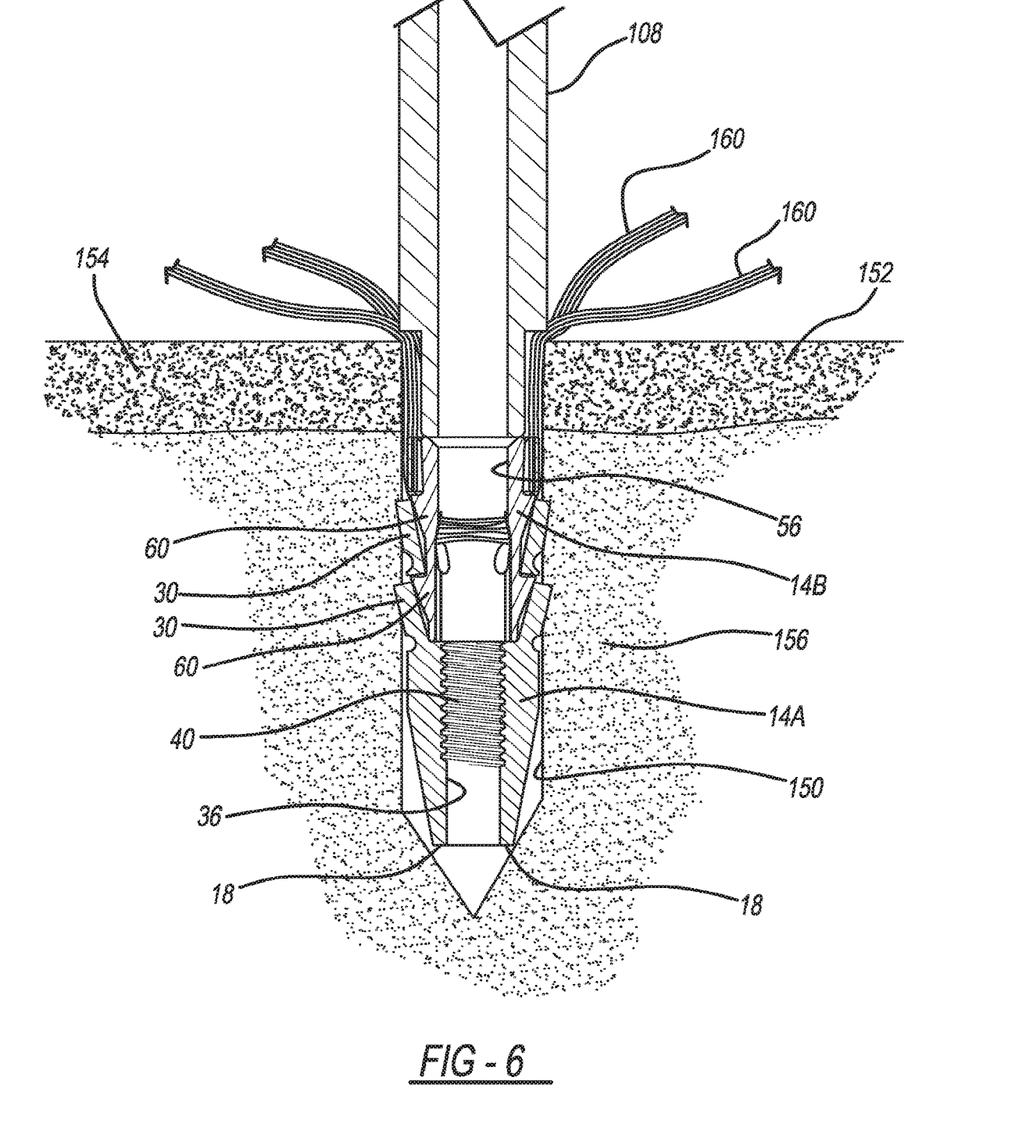
FIG. 6 is a cross-sectional view of the suture anchor anchored in bone.

With additional reference to FIGS. 5 and 6, a method of implanting the suture anchor 14 using the insertion tool 12 will now be described. With the suture anchor 14 mounted to the insertion tool 12 and the suture 160 threaded through the first pair of apertures 62A/62B and the second pair of apertures 64A/64B, the suture anchor 14 is inserted into bone hole 150. The bone hole 150 can be predrilled or the suture anchor 14 can be impacted into the bone 152 in order to form the bone hole 150 due in part to the presence of the pointed tip 118 of the inner rod 110.

The insertion tool 12 is pushed into the bone hole 150 until the annular flange 114 abuts an outer surface of the cortical bone layer 154, which results in the suture anchor 14 being positioned such that both the outer portion 14A and the inner portion 14B are arranged beyond cortical bone layer 154 and within cancellous bone layer 156. After the suture 160 and the tissue 162 are positioned and tensioned, the inner portion 14B and the outer portion 14A are brought together such that the inner portion 14B is distally inserted into the tapered proximal portion 32 of the first bore 26 of the outer portion 14A.

The inner portion 14B can be inserted into the tapered proximal portion 32 in any suitable manner. For example, the outer portion 14A and the inner portion 14B will be drawn together upon simultaneously actuating the lever 106 and pushing the elongated shaft 108 into the bone hole 150, or by pulling the elongated shaft 108 proximally, keeping annular flange 114 in contact with cortical bone layer 154. The inner portion 14B will be retained within the tapered proximal portion 32 by way of a Morse taper lock between the inner surface 24 of the outer portion 14A and the outer surface 54 of the inner portion 14B.

As the inner portion 14B enters the tapered proximal portion 32, the retention tabs 60 will force the retention fins 30 into the cancellous bone 156 surrounding the bone hole 150 to retain the suture anchor 14 within the cancellous bone 156. The suture 160 will be compressed between the inner surface 24 of the outer portion 14A and the outer surface 54 of the inner portion 14B in order to couple the suture 160 to the suture anchor 14. As the inner portion 14B enters the tapered proximal portion 32, the suture 160 will move from the first portion 66 of the apertures 62A, 62B, 64A, and 64B and into the second portion 68. Because the second portion 68 has a smaller diameter than the first portion 66, and a smaller diameter than the suture 160, the suture 160 will be compressed and tensioned within the second portion 68 between opposed walls thereof to further couple the suture 160 to the suture anchor 14. As the lever 106 is pressed further, the inner rod 110 will decouple from engagement with the first locking member 40. For example, the threads of the second locking member 120 will strip or pull away from cooperation with the threads of the first locking member 40.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of implanting a suture anchor into a bone hole comprising:
    inserting a suture anchor into the bone hole with an insertion tool, the suture anchor includes an outer anchor part and an inner anchor part that are decoupled during insertion; and
    coupling the outer anchor part and the inner anchor part with a plurality of taper locks between a plurality of tapered outer surfaces of the inner anchor part and a plurality of tapered inner surfaces of the outer anchor part, a suture extending through a first pair of opposing apertures defined in the inner anchor part is compressed between the outer anchor part and the inner anchor part to retain the suture to the suture anchor.

2. The method of claim 1, further comprising connecting the suture to tissue before or after inserting the suture anchor in bone.

3. The method of claim 1, further comprising moving retention fins of the outer anchor part into contact with an inner surface of the bone hole by moving retention tabs of the inner anchor part into contact with the retention fins.

4. The method of claim 3, further comprising coupling the outer anchor part and the inner anchor part such that the suture extending through the opposing apertures moves from a first portion of the apertures to a second portion of the apertures that is more narrow than the first portion to compress the suture in the second portion and retain the suture in cooperation with the suture anchor.

5. The method claim 3, further comprising coupling the outer anchor part and the inner anchor part by merging the outer anchor part and the inner anchor part together with the insertion tool coupled to a locking member of the outer anchor part.

6. The method of claim 3, wherein the plurality of taper locks are formed by a plurality of retention fins along the tapered inner surface of the outer anchor part and a plurality of retention tabs along the tapered outer surface of the inner anchor part.

7. A method of implanting a suture anchor into a bone hole comprising:
    coupling a suture anchor to an insertion tool, wherein the suture anchor includes an outer anchor part and an inner anchor part, and wherein the insertion tool is coupled via a locking member to the outer anchor part at a distal end thereof and the inner anchor part is moveable distally along the insertion tool;
    inserting the suture anchor into the bone hole with the insertion tool, the outer anchor part and the inner anchor part are decoupled during insertion;
    coupling the outer anchor part and the inner anchor part with a taper lock between a tapered outer surface of the inner anchor part and a tapered inner surface of the outer anchor part, a suture extending through a first pair of opposing apertures defined in the inner anchor part is compressed between the outer anchor part and the inner anchor part to retain the suture to the suture anchor;

decoupling the insertion tool from the suture anchor by decoupling the locking member; and removing the insertion tool through a bore in the inner anchor part.

8. The method of claim 7, further comprising connecting the suture to tissue before or after inserting the suture anchor in bone.

9. The method of claim 7, further comprising moving retention fins of the outer anchor part into contact with an inner surface of the bone hole by moving retention tabs of the inner anchor part into contact with the retention fins.

10. The method of claim 9, further comprising coupling the outer anchor part and the inner anchor part such that the suture extending through the opposing apertures moves from a first portion of the apertures to a second portion of the apertures that is more narrow than the first portion to compress the suture in the second portion and retain the suture in cooperation with the suture anchor.

11. The method claim 7, further comprising coupling the outer anchor part and the inner anchor part by merging the outer anchor part and the inner anchor part together with the insertion tool coupled to the locking member of the outer anchor part.

12. The method of claim 7, wherein the taper lock comprises a plurality of taper locks that are formed by a plurality of retention fins along the tapered inner surface of the outer anchor part and a plurality of retention tabs along the tapered outer surface of the inner anchor part.

13. A method of implanting a suture anchor into a bone hole comprising:

coupling a suture anchor to an insertion tool, wherein the suture anchor includes an outer anchor part and an inner anchor part, and wherein the insertion tool is coupled via a locking member to the outer anchor part at a distal end thereof;

inserting the suture anchor into the bone hole with the insertion tool, the outer anchor part and the inner anchor part are decoupled during insertion;

coupling the outer anchor part and the inner anchor part with a plurality of taper locks between a plurality of tapered outer surfaces of the inner anchor part and a plurality of tapered inner surfaces of the outer anchor part, whereby the act of coupling the outer anchor part and the inner anchor part moves retention fins of the outer anchor part into contact with an inner surface of the bone hole by moving retention tabs of the inner anchor part into contact with the retention fins;

decoupling the insertion tool from the suture anchor by decoupling the locking member; and removing the insertion tool through a bore in the inner anchor part.

14. The method of claim 13, wherein the taper lock comprises a plurality of taper locks that are formed by the plurality of retention fins along the tapered inner surface of the outer anchor part and the plurality of retention tabs along the tapered outer surface of the inner anchor part.

15. The method of claim 13, further comprising connecting a suture to tissue before or after inserting the suture anchor in bone.

* * * * *

UNITED STATES PATENT AND TRADEMARK OFFICE
CERTIFICATE OF CORRECTION

PATENT NO. : 10,201,344 B2
APPLICATION NO. : 15/210248
DATED : February 12, 2019
INVENTOR(S) : Christopher Palese Page 1 of 1

It is certified that error appears in the above-identified patent and that said Letters Patent is hereby corrected as shown below:

In the Claims

In Column 6, Line 39, in Claim 5, after "method", insert --of--

In Column 7, Line 19, in Claim 11, after "method", insert --of--

Signed and Sealed this
Fourteenth Day of April, 2020

Andrei Iancu
*Director of the United States Patent and Trademark Office*